United States Patent [19]
Badano et al.

[11] Patent Number: 6,167,292
[45] Date of Patent: Dec. 26, 2000

[54] REGISTERING METHOD AND APPARATUS FOR ROBOTIC SURGERY, AND A REGISTERING DEVICE CONSTITUTING AN APPLICATION THEREOF

[75] Inventors: Fernand Badano, Villeurbanne, France; Jörg Fischer, Chemnitz, Germany

[73] Assignees: Integrated Surgical Systems SA, Bron, France; Fischer-Schnappauf-Stockmann GbR, Chemnitz, Germany

[21] Appl. No.: 09/169,450

[22] Filed: Oct. 9, 1998

[30] Foreign Application Priority Data

Jun. 9, 1998 [FR] France .................................. 98 07234

[51] Int. Cl.[7] .................................................. A61B 5/05
[52] U.S. Cl. ...................... 600/407; 600/427; 600/429; 600/439; 606/2; 606/13; 606/130
[58] Field of Search ....................................... 600/310, 407, 600/409, 414, 417, 423, 426, 429, 437, 463, 476, 425, 411; 604/513; 606/2, 13, 130

[56] References Cited

U.S. PATENT DOCUMENTS

| | | | |
|---|---|---|---|
| 5,299,288 | 3/1994 | Glassman et al. | 395/80 |
| 5,394,457 | 2/1995 | Leibinger et al. | 378/162 |
| 5,515,853 | 5/1996 | Smith et al. | 128/661.01 |
| 5,617,857 | 4/1997 | Chader et al. | 128/653.1 |
| 5,622,170 | 4/1997 | Schulz | 128/653.1 |
| 5,630,431 | 5/1997 | Taylor | 128/897 |
| 5,749,362 | 5/1998 | Funda et al. | 600/407 |
| 5,807,252 | 9/1998 | Hassfeld et al. | 600/407 |
| 5,891,034 | 4/1999 | Bucholz | 600/426 |
| 5,951,475 | 9/1999 | Gueziec et al. | 600/425 |
| 5,954,647 | 9/1999 | Bova et al. | 600/407 |
| 5,978,696 | 11/1999 | VomLehn et al. | 600/411 |

FOREIGN PATENT DOCUMENTS

| | | | |
|---|---|---|---|
| 0 591 712 A1 | 4/1994 | European Pat. Off. | A61B 19/00 |
| 0 832 609 A2 | 4/1998 | European Pat. Off. | A61B 17/32 |
| 195 06 197 A1 | 9/1996 | Germany | A61B 5/103 |
| WO 94/17733 | 8/1994 | WIPO | A61B 6/12 |
| WO 96/11624 | 4/1996 | WIPO . | |
| WO 97/40766 | 11/1997 | WIPO | A61B 19/00 |

*Primary Examiner*—Marvin M. Lateef
*Assistant Examiner*—Jeoyuh Lin
*Attorney, Agent, or Firm*—Cohen, Pontani, Lieberman & Pavane

[57] ABSTRACT

The invention relates to a device for bringing into register for robotic surgery. The device having at least one insert designed to receive at least two distinct support elements, specifically a first support element having at least three marker elements disposed in a non-aligned spaced-apart configuration and made of a material that shows up in an image made with an appropriate imaging device; and a second support element having at least three energy-emitting or receiving elements likewise disposed in a non-aligned spaced-apart configuration. The invention serves to bring equipment for robotic surgery into register in a manner that is simple, safe, and reliable.

24 Claims, 4 Drawing Sheets

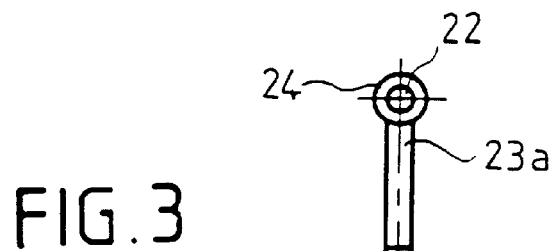
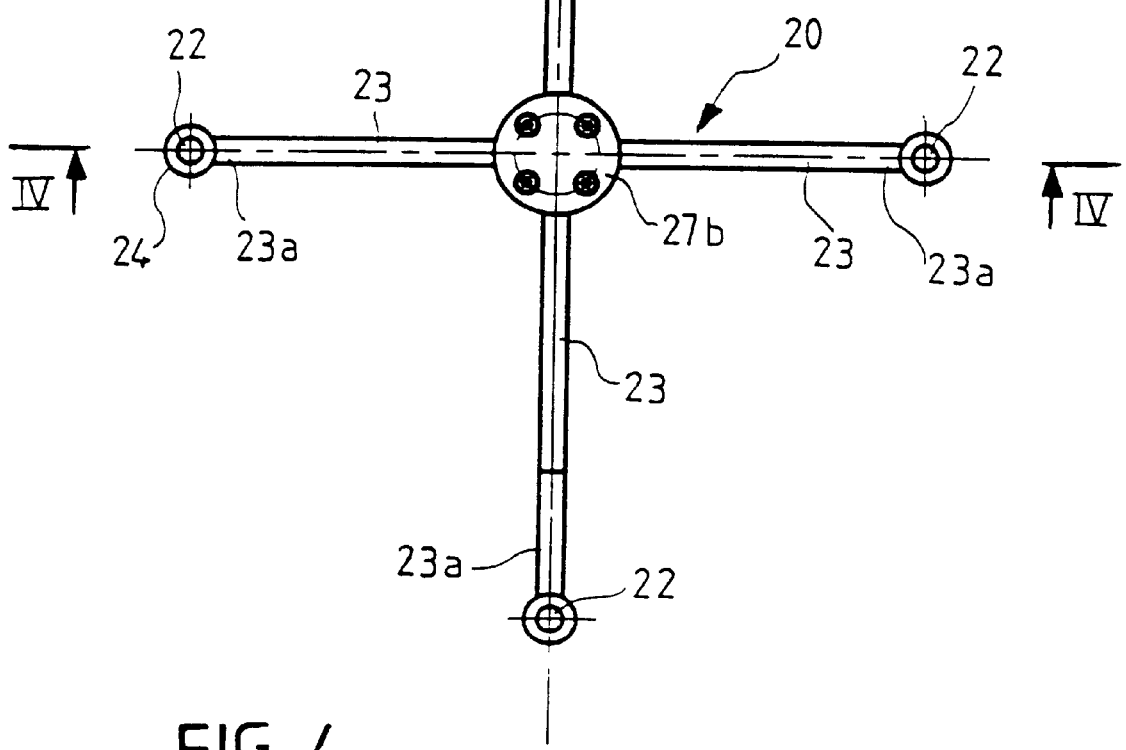
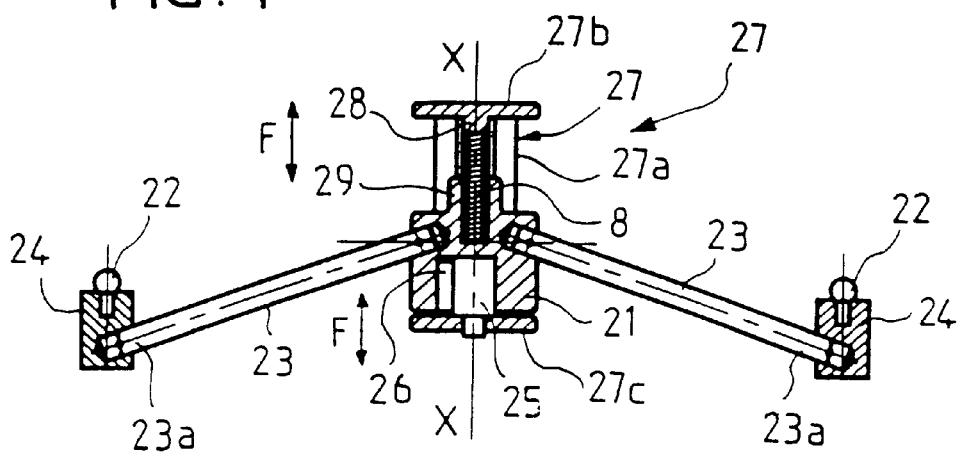

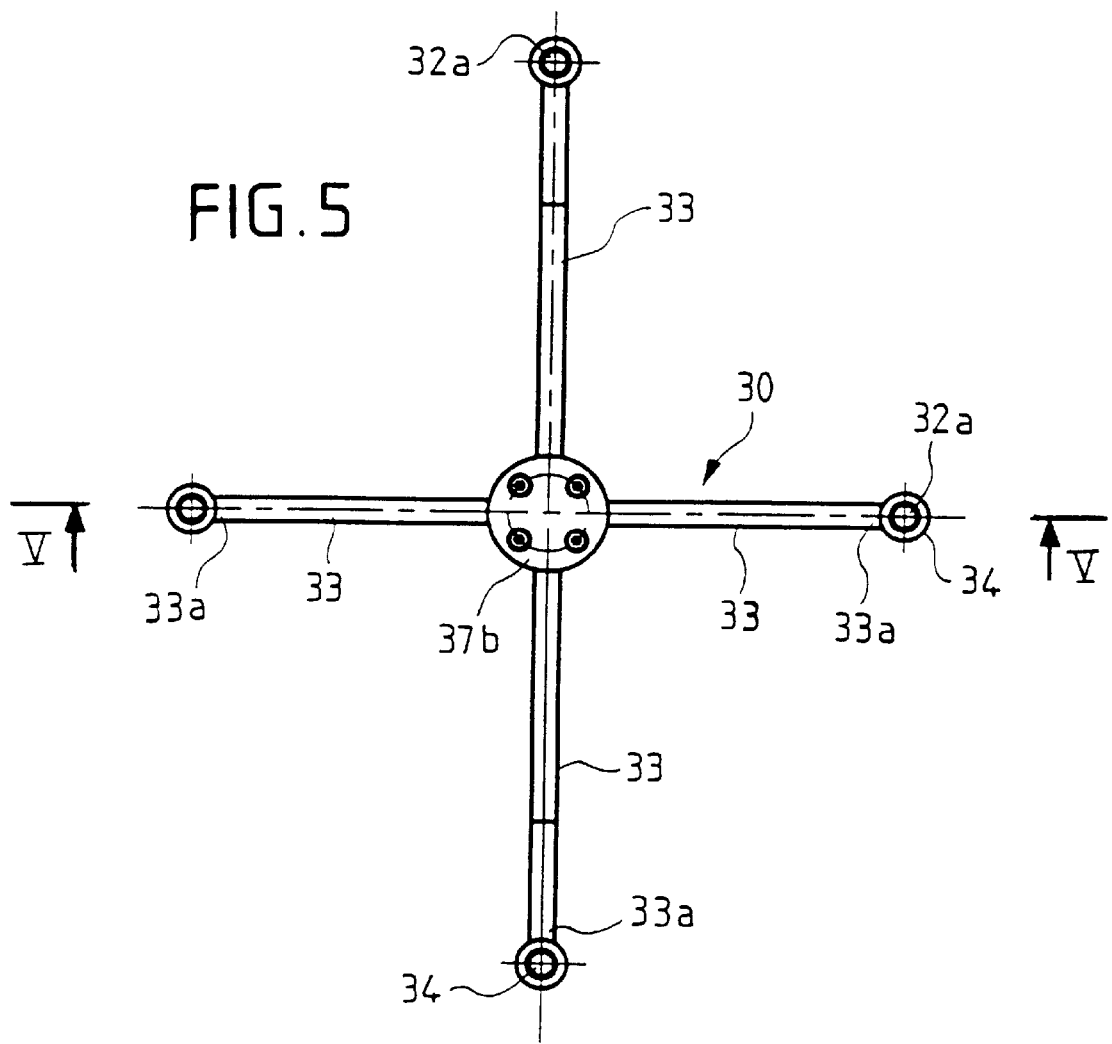
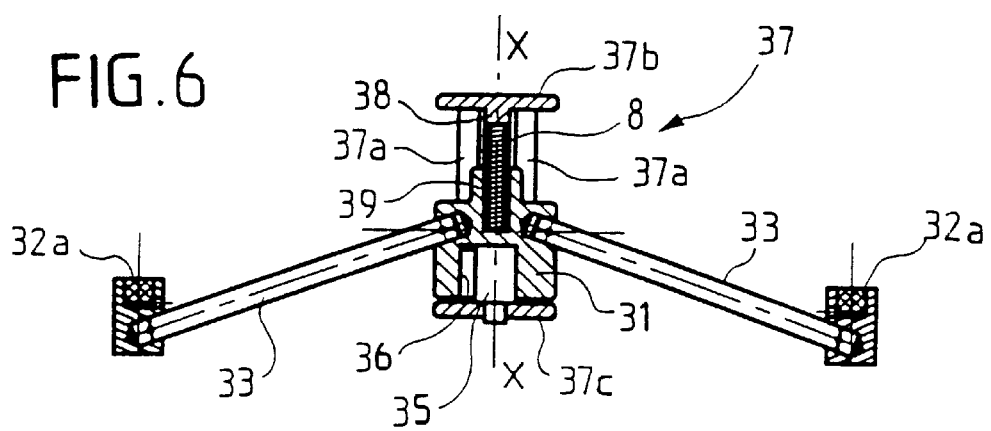

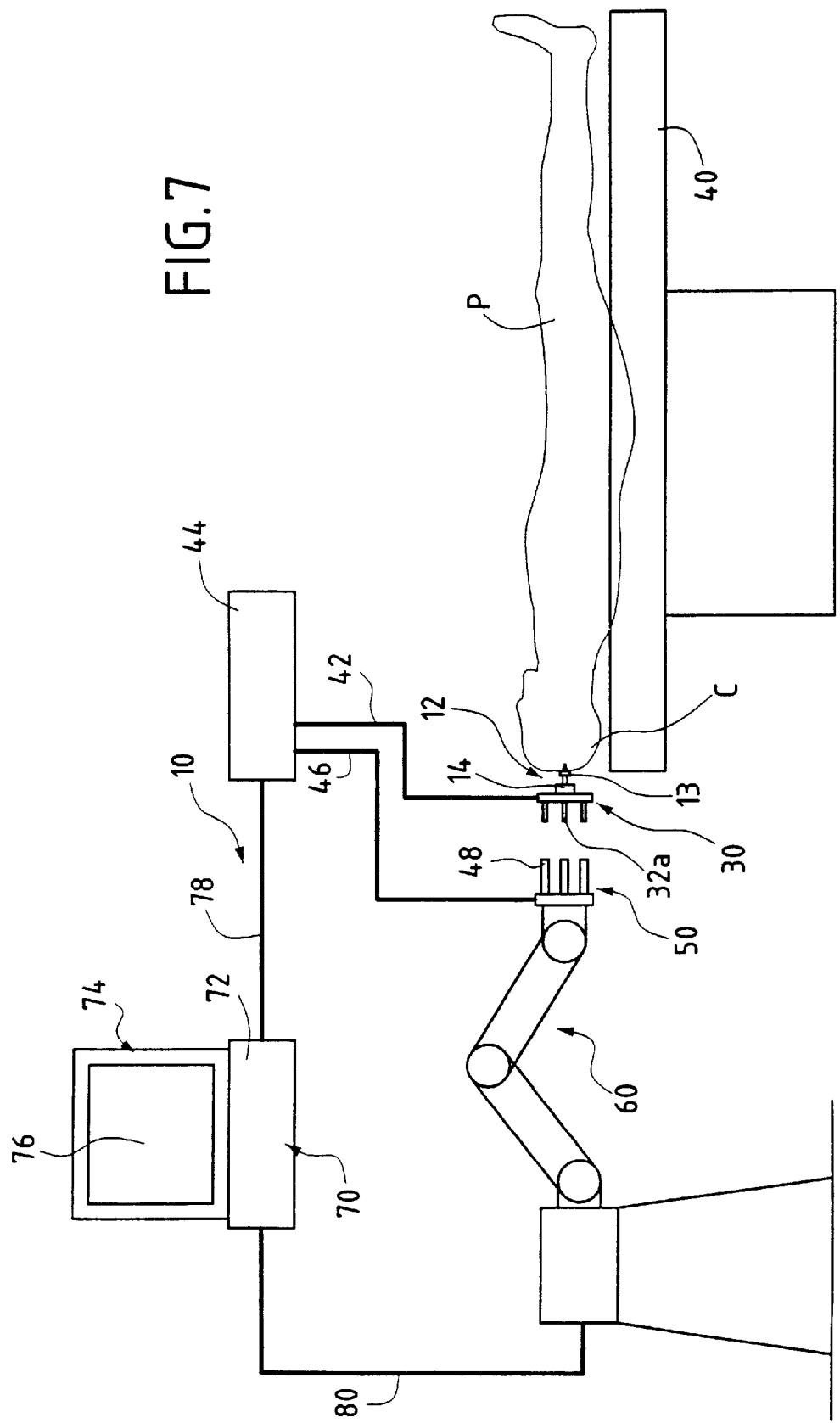

REGISTERING METHOD AND APPARATUS FOR ROBOTIC SURGERY, AND A REGISTERING DEVICE CONSTITUTING AN APPLICATION THEREOF

The present invention relates essentially to a method and to apparatus for bringing into register for use in robotic surgery, and it also relates to a device for bringing into register that constitutes an application thereof.

More particularly, the invention relates to a method and to apparatus, and also to a device, making it possible to bring anatomic structures of a patient into register with a robotic system for providing assistance in surgery under the guidance of preoperative images such as conventional radiological examinations, CT scanner examinations, magnetic resonance imaging (MRI), or positron emission tomography (PET) imaging. The device is made up of energy emitter/receivers, imaging markers, and a signal processing unit. The markers are adapted to various types of imaging and provide high contrast; they are placed on the patient in a predetermined three-dimensional disposition in the vicinity of the anatomic region of interest on a portion of the body that provides positioning that is stable over time (e.g. a bone structure). The examination performed by the imaging shows the anatomy of the patient together with the markers whose coordinates can be defined in the frame of reference of the images by various image processing means. Before beginning surgery, the energy emitter/receivers are mounted to take the place of the markers. The robot for providing assistance in surgery is also fitted with energy emitter/receivers. By processing the signals emitted thereby it is possible to locate the coordinates of the emitter/receivers on the patient in the frame of reference of the robot. Since the disposition in three dimensions of the emitter/receivers is the same as that of the markers, the anatomic structures can be located by the robot by bringing the coordinates of the markers in the frame of reference of the image into register with the emitter/receivers in the frame of reference of the robot.

1. Field of the Invention

The invention lies in the field of image-guided robotic surgery. The invention relates to a device serving to bring into register the anatomic structures of a patient and a robotic system for providing assistance in surgery under the guidance of preoperative images such as conventional radiological examinations, CT scanner examinations, nuclear magnetic resonance imaging (NMRI), or positron emission tomography (PET) imaging. The device is made up of energy emitter/receivers, imaging markers, and a signal processing unit.

2. State of the Art

Image-guided surgery is a new approach seeking to improve the clinical results of surgery and to implement new operational techniques for the benefit of the patient. This approach is particularly applicable to neurosurgery and to orthopedic surgery: its consists in planning the action which is the best from a clinical point of view on the basis of preoperative images, and then, in the operating theater, in performing the operation in application of the pre-established plan. The plan requires tools to be positioned fiery accurately in three dimensions and it also requires manipulation to be performed with a high degree of dexterity. One of the difficulties encountered in implementing image-guided surgery is bringing into register the operative field (or "patient space") and the plan shown on the preoperative images (or "image space"). It turns out to be particularly difficult for surgeons to perform such bringing into register when the surgical action takes place in three dimensions.

Image-guided surgery is implemented by using tools during the operation to assist the surgeon in executing the plan. These tools can be of various kinds, and are commonly known as "navigation systems". Navigation systems help the surgeon by bringing into register automatically on the basis of special procedures using three-dimensional location sensors. By using markers that are visible in the images and that can be located by sensors during the operation, such systems are capable of displaying, on the preoperative images, the position of an instrument so as to guide the surgeon in performing the planned surgery. The procedure for bringing into register requires intervention from the surgeon to locate in patient space the markers that are visible in the images, and it is that which makes such a system difficult to implement. In addition, the action of the surgeon in bringing the systems into register can be a source of error, thereby impairing accuracy, and thus the clinical results of the operation. Navigation systems can also include robotic assistance for performing the action: the robot which is preprogrammed to implement the plan drawn up before the operation positions and manipulates the tools required for the operation with great accuracy. Robotic assistance likewise requires the robot to be brought into register with the patient space, and that is performed by using procedures similar to those used in navigation systems. It should be emphasized, that with robotic systems, the robot itself is sometimes used as a three-dimensional sensor, however that technique is not applicable when the anatomic structures are not fixed in three dimensions throughout the operation.

In order to exploit its potential to the full, image-guided surgery requires robotic assistance including real-time assistance for bringing into register. This makes it possible to follow movements of the portions of the body on which the operation is being performed. Presently employed systems make use of optical sensors (infrared emitters are located by CCD cameras), mechanical sensors, magnetic sensors, or indeed ultrasound sensors. Optical sensors are complex and bulky and require both the position of the patient and the position of the robotic arm to be measured. In addition, the space between the emitters and the cameras must be clear so that the optical link can function. Mechanical sensors also clutter the operative field and require procedures for bringing into register that are lengthy and highly dependent on the operator. Magnetic sensors make it possible to locate the position of a tool in three-dimensional space, but they are highly sensitive to disturbances of the magnetic field.

Ultrasound measurement systems are commonly used in numerous three-dimensional measurement applications. Such systems operate by measuring the travel time between an ultrasound emitter and an ultrasound receiver, thereby making it possible to calculate the distance travelled, given the propagation speed of ultrasound in air. The numerous emitters and receivers make it possible, by triangulation calculations, to perform three-dimensional measurements. Ultrasound measurement systems are compact and relatively low cost, however their accuracy is affected by variations of air temperature and they are sensitive to ambient disturbances.

Ultrasound systems are already in use in the field of image-guided surgery for bringing patient space into register with image space. In particular, certain "navigators" are equipped therewith: in most cases they comprise a ring having a multiplicity of receivers which receive signals coming from emitters mounted on special tools. The tools are attached either to an anatomic structure of the patient, or to the tools for performing the surgical intervention, or else to pointers. That disposition requires that the distances between the emitters and the receivers are about 2 meters (m), and thus are relatively long (thereby increasing potential errors of measurement), and the surgeon must take action to locate the imaging markers (generally by means of a pointer) so that the image and the patient can be brought into register.

Representative examples of the prior art as described above are as follows:

Firstly, document U.S. Pat. No. 5,078,140 relates to a robotic stereoaxis system assisted by an imaging device. That device would appear to be more suitable for surgery on body elements that are practically stationary throughout the operation, as is generally the case for an operation performed on the brain. However, that device does not appear to be adapted to surgery in which the body elements are capable of moving during the surgical procedure.

Document WO-A-96/11624 discloses a surgical navigation system including localization and reference frames. For the procedure described in that document, anatomic reference points are initially used to create preprocedure images of the anatomic structure on which the surgical procedure is to be performed.

At the beginning of the operation, a mechanical system supporting a plurality of emitters is fixed directly or indirectly to a portion of the body which is tied to the anatomic structure where the operation is to be performed.

Thereafter, the emitters are caused to emit signals which are received by receivers disposed facing them and at a certain distance therefrom. The signals received by the receiver devices are then processed to locate in three dimensions each of the emitters, and thus to locate the support system, thereby defining the frames of reference in the three-dimensional coordinate system of the patient in which the operation actually takes place, and which is thus anchored relative to the anatomic structure in which the operation is to be performed. It will be observed that this reference system can be located at any time during the surgical procedure.

Thereafter, it is necessary in the context of that prior document to bring the reference system defined by the emitter support system into register with the anatomic structure itself visible on the preprocedure images.

That operation of bringing into register requires a pointer to be used which also has emitters and which is pointed to each of the anatomic reference points in order to enable them to be located by computation in the reference system defined by the emitter support system.

In practice that means that the emitter support system is also brought into register with the body elements of the anatomic structure on which the surgical operation is to be performed. It is thus possible continuously to track the position in real time of the anatomic structure on which the operation is to be performed by means of the emitters of the support system.

On page 22, at line et seq., that document envisages, in certain situations, replacing the above-mentioned anatomic reference points by markers or "fiducials" e.g. fixed to the surface of the skin, enabling the given set of preprocedure images to be transformed into a given set of displaced images, i.e. images of the operating field.

In both cases, whether use is made of anatomic reference points or of markers disposed on the surface of the body such as on the surface of the skin, the reference points always require a subsequent operation of bringing the emitter support system into register with the anatomic structure on which the operation is to be performed and which may have reference points, either directly or indirectly.

That procedure for bringing into register is lengthy and complicated. It therefore needs to be avoided by surgeons since it runs the risk of leading to errors which, if ever they result in incorrect surgical operations, are entirely prejudicial to the health of the patient.

During the procedure, it is possible to replace the markers or fiducials by emitters (page 27, lines 19–20). According to that document, it is recommended to keep the body of the patient in a frame which enables accurate positioning to be implemented and which includes displacement mechanisms making it possible to ensure that the exact positions of the emitters during the procedure are compared with the positions of the markers in the preprocedure images. In other words, it is desired at the time of the operation to impart a geometrical position for the anatomic structure that in identical to its position as defined by the preprocedure images, thereby attempting to simplify the procedure by superposing the preprocedure images with the real images made during the operation (see the explanation at page 27, lines 21–30).

Unfortunately, that method assumes that the frame which supports the body is perfect. Unfortunately, that is far from being the case. In addition, the markers which are disposed on the surface of the skin for positioning the underlying anatomic structure on which the operation is to be performed, provide positioning that is far from perfect.

Thereafter, and in more anecdotal manner, the surgical instrument proper needs to be positioned in the frame of reference as defined above. Under such circumstances, it is generally recommended to mount a plurality of emitters on the body of the surgical instrument, with the emitters being in known relationship to the working head of the instrument.

During emission by one of the emitters tied to the surgical instrument, the detectors will receive the emission and will enable the exact position of the head of the surgical instrument to be calculated in the frame of reference that has just been defined. This portion is described in that document on page 27, line 12 to page 28, line 21, in particular.

It will be understood that as a whole that apparatus is relatively bulky and its procedure for bringing into register is complex and increases the risk of error.

SUMMARY OF THE INVENTION

A main object of the invention is to solve the novel technical problem consisting in finding a solution enabling a compact system to be provided for bringing image-guided robotic surgery into register without requiring action on the part of the surgeon and while still making action in real time possible, including tracking the movements of the patient's body while the surgical procedure itself is taking place.

Another main object of the invention is to solve the novel technical problem consisting in providing a solution making it possible radically to simplify the procedure for bringing items into register, and to minimize the risk of error.

For the first time, the present invention solves these novel technical problems in a manner that is simple, safe, and reliable, and that is reproducible on an industrial or a medical scale.

Thus, in a first aspect, the present invention provides a device for bringing into register for robotic surgery, the device comprising at least one insert designed to receive at least two distinct support elements, specifically a first support element having at least three marker elements disposed in a non-aligned spaced-apart configuration and made of a material that shows up in an image made with an appropriate imaging device; and a second support element having at least three energy-emitting or receiving elements likewise disposed in a non-aligned spaced-apart configuration.

In an advantageous embodiment of the invention, the insert is designed to receive in succession both the first and the second above-mentioned support elements, one taking the place of the other.

In another advantageous embodiment of the invention, when the second above-mentioned support element replaces the first support element on the insert, each energy-emitting or receiving element of the second element occupies a position that is substantially identical to the position of a corresponding marker element previously fixed to the insert. In practice, the focus of each emitter or receiver element lies in a position that is substantially identical to the center of gravity of each marker element.

In yet another advantageous embodiment of the invention, at least one, and preferably all, of the energy-emitting or receiving elements comprises an ultrasound energy emitter or receiver element. In this case, the emitter element is an ultrasound emitter element, e.g. of the piezoelectric type and well known to the person skilled in the art, and the ultrasound receiver element comprises at least one microphone, also well known to the person skilled in the art.

As other energy emitter/receiver elements, it is also possible to use emitter/receiver elements of energy that is infrared, optical, or electromagnetic, even though those types of energy are at present not preferred as much as ultrasonic energy. The invention covers any energy emitter or receiver elements, without restriction.

In yet another advantageous embodiment of the invention, the above-mentioned device for bringing into register has a third support element comprising at least three energy-receiving or energy-emitting elements respectively capable of being mounted in positions suitable for receiving or emitting relative to the above-mentioned second support element having the energy-emitting or energy-receiving elements respectively. Preferably, the third support element is mounted directly or indirectly to a robotic arm which preferably receives a surgical tool. In this context, it is advantageous for the positions of the energy receiver or emitter elements on said arm to be known, and also for the position of the surgical tool relative to said arm to be known, which, in practice, will be the case in order to make bringing into register easier.

In a presently preferred embodiment, the second above-mentioned support element is provided with at least three energy receiver elements, preferably elements for receiving ultrasound energy, while the third above-mentioned support element likewise comprises at least three energy emitter elements, preferably emitters of ultrasound energy, that are in a non-aligned and spaced-apart configuration.

In yet another advantageous embodiment of the invention, the first support element and the second support element are substantially identical in shape, each support element comprising a central body designed to cooperate with the above-mentioned insert and having at least three arms extending outwardly from the central body and having in the vicinity of their free ends either at least one of the above-mentioned marker elements or at least one of the above-mentioned energy-emitting or energy-receiving elements.

In yet another advantageous embodiment of the invention, the above-mentioned insert has a fixing portion for fixing to the anatomical structure where the surgical operation is to be performed, and a portion designed to be connected to the first or second above-mentioned support element. Advantageously, the connection is provided with the help of predetermined orientation means. The predetermined orientation means may, for example, comprise a mutually cooperating key and keyway system between the insert and the first or second above-mentioned support element. Advantageously, the key portion is associated with the insert while the keyway portion is defined in the structure of the first or second element, in the central body thereof.

In a second aspect, the present invention provides a method of bringing into register for preferably-robotic image-guided surgery, the method comprising a preprocedure step of taking a preprocedure image of the anatomic structure where the surgical operation is to be performed, said anatomic structure being provided with marker elements for marking the anatomic structure and visible on said image, a second step of securing an energy emission or reception system to said anatomic structure, the system comprising a plurality of energy emitter or receiver elements suitable for enabling an energy receiver or emitter system comprising a plurality of energy receiver or emitter elements to pick up data relating to the positions in three dimensions of the energy emitter or receiver elements; and a third step of bringing the positions of the energy emitter receiver elements into register with the positions of the marker elements in the preprocedure image, thereby enabling a surgeon subsequently to follow a preprogrammed surgical approach on the preprocedure image, wherein:

a) a prior operation is performed of fixing at least one device comprising at least one insert on at least one zone of the anatomic structure, said insert being designed to receive at least two separate support elements, namely a first support element having at least three marker elements disposed in a non-aligned and spaced-apart configuration and made out of a material that shows up in an image made with an appropriate imaging device; and a second support element having at least three energy emitter or receiver elements disposed in a non-aligned and spaced-apart configuration, thus constituting the above-mentioned emitter or receiver system;

b) on each insert, said first element having said at least three marker elements is mounted and a preprocedure image is taken with an appropriate imagine device, which image is stored and preferably displayed on an image display device;

c) said first element on said insert is replaced by said second element so that each emitter or receiver element of the second support element is to be found in a position that is essentially identical to a position occupied by a respective marker element previously fixed to the insert;

d) a third support element, constituting the above-mentioned receiver or emitter system, is provided that has at least three energy receiver or emitter elements respectively in positions suitable for receiving or emitting relative to the second support element, in register with the respective emitter or receiver elements of the second support element;

e) energy is emitted by each emitter element and is received by each receiver element, and the data from receiving said emission is recorded;

f) said recording of energy emission data is processed to determine the positions in three dimensions of the emitter or receiver elements which are substantially identical to the positions of the marker elements that have been recorded and that define a unique reference system for the anatomic structure; and g) finally, said second support element is preferably left in place on said insert to bring the emitter/receivers into register in real time with the marker elements that defined the initial reference system in the preprocedure image.

Naturally, in the context of this method, various implementations can be derived from the embodiments relating to the device for bringing into register.

In particular, it is preferable in the context of the invention for the the third support element to be directly or indirectly mounted on a robotic arm that preferably receives the surgical tool.

In a third aspect, the present invention also provides apparatus for bringing into register, the apparatus comprising at least one device for bringing into register as defined above, the apparatus comprising at least one above-mentioned insert, at least two distinct support elements namely a first support element comprising at least three marker elements, and at least one second support element comprising at least three energy emitter or receiver elements, and also at least one third support element preferably mounted directly or indirectly on a robotic arm, together with a unit comprising means for processing signals emitted and then received by the energy receivers serving to locate the coordinates of the emitter/receivers on a patient in the frame of reference of the robotic arm and subsequently enabling the coordinates of the marker elements in the frame of reference of the preprocedure images taken with the appropriate imaging device and recorded on the image recording means and preferably displayed by image display means to be brought into register.

In an advantageous embodiment of the invention, the apparatus comprises a central control unit having calculation means such as a microcomputer, and connected respectively to the signal processing means and to the robotic arm and also enabling a surgical tool to be controlled and thus to be used for surgical purposes.

Other particular embodiments of the apparatus can manifestly be derived from the above description and from the following description which forms an integral portion of the present invention, and also from the figures which likewise form an integral portion of the invention.

The principle of the invention relies on causing energy emitters/receivers to take the places of the imaging markers, and on combining them with other emitter/receivers preferably mounted directly on the robotic arm that is to be brought into register with patient space. This disposition presents the following advantages:

localization of the imaging markers as is required for the calculations involved in bringing into register does not require any intervention on the part of the surgeon;

the patient is located in three dimensions directly from the device carrying the operating instrument (i.e. the robot);

by having the emitter/receivers mounted directly on the tool that is to be brought into register, the emitter/receiver measurement distances are about 20 cm, i.e. they are short, thereby making it possible to achieve greater measurement accuracy compared with other configurations;

it is possible to track in real time the movements of the anatomic structures on which the markers are fixed; and bulk is reduced.

General Implementation of the Invention

One possible implementation of the invention is described below.

The system, which is intended for robotic surgery of the brain and which is guided by preoperative images, is made up of: an insert having a prismatic endpiece; two identical support elements, in this case frames, which can be attached to said insert (one of the support elements carrying imaging markers while the other has energy receiver elements, in this case preferably microphones, at the same locations as the markers); a set of at least three energy emitters, preferably emitters of ultrasound, disposed in a known configuration for mounting on the surgical robot; and also having a data processor unit.

The insert with a prismatic endpiece is made of a biocompatible material that does not disturb the various imaging systems that may be used (CT, MRI, PET, X-rays, it being possible for each imaging means to have a matching type of insert). The insert makes it possible for the frames to be repositioned accurately while ensuring that they are highly stable while in use. The frames can be made out of lightweight material, possibly being suitable for sterilization, that does not disturb the various imaging systems (each imaging system having a most appropriate material). The geometry of the frames is such that the centers of gravity of the imaging markers coincide with the focuses of the microphones. The set of ultrasonic emitters mounted on the robot is of known dimensions so as to be able to perform triangulation calculations.

The principle of the operation is set out in the following paragraphs.

First Stage: Imaging Examination
  a) the insert is put into place in a localized zone on the head of the patient, and is securely anchored in the bone of the skull close to the anatomic regions where the operation is to be performed;
  b) the frame is constituted in this case by the first support element carrying the appropriate imaging markers is now attached to the insert;
  c) imaging examination is performed (CR, MRI, PET or X-rays); the images obtained must show the imaging markers; and
  d) the frame can then be removed, while leaving the insert in place.

Second Stage: Location of the Imaging Markers by the Robot
  a) the frame now constituted by the second support element carrying the microphones is attached to the insert;
  b) the ultrasonic emitters are mounted on the robot;
  c) the robot is put into its configuration such that its ultrasound emitter/receivers are close to the frame;
  d) the emitters and the microphones are connected to the data processing unit; and
  e) measurements giving the positions of the markers are performed by said unit.

Third Stage: Bringing Patient Space into Register with Image Space
  a) points corresponding to the center of the gravity of the image markers are secured to the anatomic structure on which surgery is to be performed;
  b) the coordinates of the image markers in the frame of reference belonging to the images are determined by the image processing means;
  c) also, since the positions of the ultrasound emitters are known by the robot, the coordinates of the microphones obtained by the data processing unit can be re-expressed in the frame of reference of the robot by mere transformation;
  d) the coordinates of the markers (or the microphones) in the frame of reference of the images and in the frame of reference of the robot are compared making it possible to bring patient space (in which the surgical instruments need to be positioned and handled) into register with image space (in which the surgery plan has been drawn up). The transformation performed in this way makes it possible to express the coordinates of any point of the anatomic structure in the image frame of reference using coordinates in the robot frame of reference. This is the information which the robot needs in order to be able to position and manipulate the surgical tools in patient space using a pre-established plan. It should be emphasized that the inverse transformation (i.e. the transformation making it possible to go from patient space to image space) is also easily calculated on the basis of the first transformation; and e) since the measurements performed by the ultrasound system are performed continuously, said transformations can be updated on a continuous basis so as to ensure that registration is updated "in real time" (in other words to ensure that account is taken of any movements in three dimensions of the anatomic structure relative to the robot).

As an alternative, points a) to d) of this third stage of the method can be implemented as follows:

a) information concerning the plan of operation can be expressed in a new frame of reference defined by the centers of gravity of the imaging markers;

b) the positions of the microphones can be measured and the coordinates of said positions in robot space can be calculated given that the positions of the ultrasound emitters are known;

c) the transformation that enables an arbitrary point in the frame of reference defined by the imaging markers to be expressed in the frame of reference of the robot is calculated; and d) this transformation is used to bring patient space and image space into register.

DETAILED DESCRIPTION OF THE DRAWINGS

FIG. 3 is a plan view of a first support element of the present invention constituting a frame, without imaging markers, designed to be fixed in removable manner on the insert shown in FIGS. 1 and 2;

FIG. 4 is a section view on line IV—IV of FIG. 3;

FIG. 5 is a view similar to FIG. 3 showing a second support element of the invention having at least three (in this case four) energy-receiving elements, said second element also being suitable for and designed to be mounted in removable manner on the insert of FIGS. 1 and 2;

FIG. 6 is a view similar to FIG. 4 on line V—V of FIG. 5; and

FIG. 7 shows surgical apparatus comprising apparatus of the present invention for bringing into register, and incorporating a device as described with reference to FIGS. 1 to 6 for bringing into register.

Figure 1:
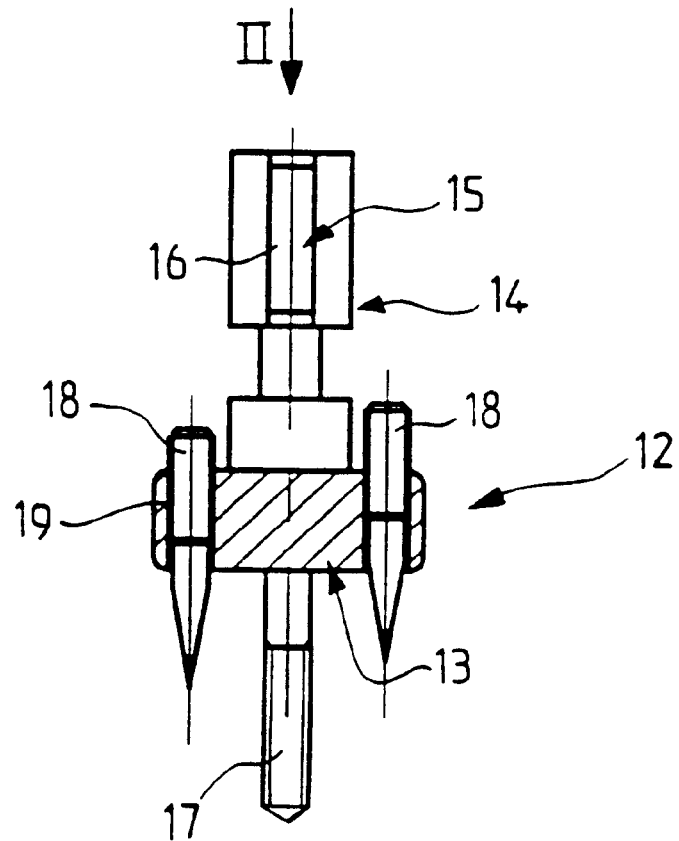
FIG. 1 is a side view in elevation of an insert of the present invention for fixing in particular to a bone of the patient, e.g. to the skull of the patient.
Figure 2:
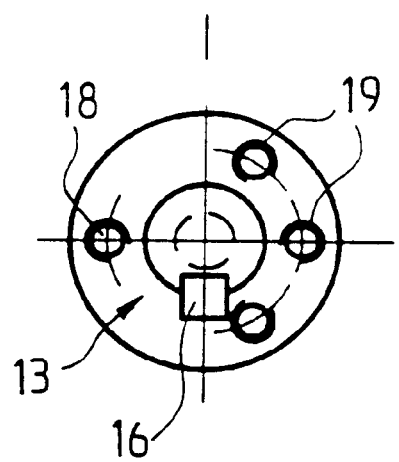
FIG. 2 is a plan view of the FIG. 1 insert seen along arrow II of FIG. 1.

With reference to FIGS. 1 and 2, a device of the present invention for bringing into register for robotic surgery is given overall reference numeral 10 in FIG. 7. This device comprising at least one insert given overall reference numeral 12, visible individually in FIGS. 1 and 2, and designed to receive at least two distinct support elements respectively designated by overall reference numeral 20 in FIGS. 3 and 4 and 30 in FIGS. 5 and 6, which are described in greater detail below.

In an advantageous embodiment, the insert 12 shown in FIGS. 1 and 2 is designed to receive in succession, each taking the place of the other: the first support element 20 of FIGS. 3 and 4; and the second support element 30 of FIGS. 5 and 6, as will easily be understood by a person skilled in the art.

In an advantageous embodiment of the invention that is presently preferred, the insert 12 comprises a fixing portion 13 for fixing to the anatomical structure where the surgical operation is to take place, as shown in FIG. 7, and a portion given overall reference numeral 14 that is designed to be connected with the first support element 20 or with the second support element 30, as mentioned above. Advantageously, this connection takes place via the portion 14 which constitutes a connection head and with the help of means 15 of predetermined orientation. By way of example, these means 15 of predetermined orientation can comprise a key-and-keyway system co-operating between the insert 12 and the first or second above-mentioned support element 20 or 30. Advantageously, the key portion 16 is associated with the insert 12 while the keyway portion 26 (FIG. 4) or 36 (FIG. 6) is defined respectively in the central body 21 of the structure of the first support element 20 or in the central body 31 of the structure of the second support element 30. It will be understood that the insert 12 can be fixed to the anatomical structure firstly by the possibly self-tapping threaded end 17 which makes it possible to achieve quick and secure installation in the bone of the skull, and secondly by fixing elements 18, such as nails or screws for example as are well known to the person skilled in the art, sliding through orifices 19 provided in the central body 13 of the insert 12.

With reference to FIGS. 3 and 4, there can be seen a presently preferred embodiment of a first support element 20 designed to be mountable in temporary manner (i.e. to be dismountable) on the insert shown in FIGS. 1 and 2. This first support element 20 comprises at least three marker elements 22 (in this case, by way of example, four marker elements 22) that are disposed in a spaced-apart and non-aligned configuration, and that are made out of a material that shows up in an image made with an appropriate imaging device. By way of example, these marker elements may be made out of an opaque stainless metal which is visible in an image made using an imaging device such as a scanner.

When using an MRI imaging device, the marker elements comprise respective cavities filled with a liquid that can be seen in the image, e.g. containing gadolidium, as is well known to the person skilled in the art.

The first support element 20 comprises a central body 21 designed to cooperate with the insert and having means for securing it in temporary manner with the insert 12, which means comprise, for example, a coaxial orifice 25 and a keyway 26 in the wall of the central body 21 which are designed to cooperate respectively with the corresponding portion 14 of the insert 12 and its key 16. It will be understood that the first support element 20 is secured in temporary manner to the insert 12 by engaging and snap-fastening the portion 14 together with its key 16 inside the opening 25 and the keyway 26, with this connection being safe and reliable until it is deliberately disconnected.

Extending from the central body 21, the first support element 20 has at least three arms 23 that project outwards from the central body 21 and that have in the vicinity of their free ends 23a respective members 24 each suitable for receiving at least ore marker element 22. The structure and the shape of this first support element as shown in FIGS. 3 and 4 constitutes an integral portion of the present invention. The arms 23 are disposed asymmetrically so as to facilitate recognition during processing.

The central body 21 carries a member 27 for temporary connection comprising two cups 27b and 27c that are interconnected by rods 27a extending substantially parallel to the axis of symmetry X—X of the central body 21. Thus, the cups 27b and 27c are disposed substantially perpendicularly relative to the rod 27a. The rods 27a are of a length that is greater than the total axial size of the central body 21, as can be seen clearly in FIG. 4. One of the cups, in this case the cup 27b remote from the keyway 26, has an extension 28 substantially coaxial with the axis X—X and cooperating with a coaxial orifice 29 provided in the central body 21 of the support element 20, there being a one-way thrust element such as a spring 8 mounted in the orifice 29 and outside the axial extension 28 so as to urge the connection member 27 continuously towards the position shown in FIG. 4.

It will be understood that to connect; the support element 20 with the insert 12, the operator presses on the cup 27b to move it downwards as represented by arrow F, thereby releasing the other cup 27c by moving it away from the space for insertion of the connection portion 14 and its key 16 in the opening 25 and the keyway 26, respectively. After insertion, releasing the top cup 27b allows the other cup 27c to rise and thus temporarily lock the portion 14 and its key 16 in the opening 25 and the keyway 26 in safe and reliable manner. It should be observed that FIGS. 1 & 2 and 3 to 6 are not to scale.

Similarly, the second support element, as shown in FIGS. 5 and 6, is preferably substantially identical in shape to the first support element 20 of FIGS. 3 and 4, as can clearly be seen by comparing FIGS. 5 and 6 with FIGS. 3 and 4.

Thus, the same reference numerals are used relative to the second support element of FIGS. 5 and 6 as are used relative to the first support element 20 of FIGS. 3 and 4, with the exception that the reference numbers are increased by ten.

However, the second support element 30, instead of having marker elements 22 has in the equivalent positions energy emitting or receiving elements, as described below.

It will be observed at this point that the second support element 30 has, at its free ends 33a, at least one energy emitter or receiver element, in this case, by way of example, an energy receiver element 32a such as a microphone, for example, assuming that the energy emitted by the emitter element is ultrasound energy, but any other kind of energy could be used, as mentioned above.

It will be understood that in a presently preferred embodiment, the second support element 30 is identical in shape to the first support element 20, thereby making it simpler to bring into register since the energy-receiving elements 32a occupy positions that are substantially identical to those occupied by the marker elements 22.

With reference to FIG. 7, there can be seen a surgical apparatus 10. In the embodiment shown, this apparatus comprises an operating table 40 on which a patient P lies ready for a surgical operation, for example, in this case, to the skull C. The apparatus 10 comprises firstly an insert 12 fixed in a localized zone on to the anatomical structure that is to be operated on. The insert 1215, for example in this case, anchored to the bone of the skull C of the patient P. Either the first support element 20 in the context of taking a preoperative image in an image-taking room, or the second support element 30 in the operating theater in the context of bringing into register may be mounted on the insert 12, as mentioned above.

It will be observed that in this case the second support element 30 is electrically connected via at least one wire 42 to a unit 44 for emitting and receiving energy and for processing the signal as emitted and then received via receiver elements 32a, said unit 44 also comprising at least one wire 46 for delivering energy to at least three elements, in this case energy-emitting elements 48, and preferably elements 48 that emit ultrasound energy and thus cooperate with microphones 32a as elements for receiving ultrasound energy.

These energy-emitting elements 48 are advantageously mounted on a third support element 50 of structure that is preferably substantially identical to the structure of the first and second support elements 20 and 30 as described above. This third support element 50 is advantageously mounted directly or indirectly on the robotic arm 60 that is well known to the person skilled in the art and that is designed subsequently to receive a surgical tool (not shown herein).

The apparatus of the invention 10 also comprises a control center 70 e.g. comprising calculation means 72 such as a computer, and image display means 74 such as a video screen 76. The control center 70 is connected by a connection cable 78 to the unit 44 and by an appropriate connection cable 80 to the robotic arm 60. It will thus be understood that the complete apparatus as shown in FIG. 7 serves to implement the above-specified method of bringing into register and also to perform general implementation of the above-specified invention.

By means of the invention, all of the above-specified technical advantages are obtained in a manner that is simple, safe, and reliable, and that can be used on an industrial or a medical scale.

The invention naturally covers all means that constitute technical equivalents of the means described, and also the various possible combinations thereof. Furthermore, the structure shown in FIGS. 1 to 7 forms an integral portion of the present invention.

What is claimed is:

1. A device for bringing images of a body part intended to be searched or submitted to surgery to register for robotic image guided search or surgery, comprising an insert arrangeable on only a localized zone of an anatomical structure and having anchoring means for anchoring said insert directly into a bone area proximate the localized zone of an anatomical structure, said insert being designed to receive successively at least two separate support elements, namely, a first support element having at least three marker elements disposed in non-aligned and spaced-apart configuration and comprising a material that shows up in an image produced with an imaging device, and a second support element having at least three energy emitter or receiver elements disposed in a non-aligned and spaced-apart configuration, each energy emitter or receiver element of the second support element, when in place on the insert, in replacement of the first support element, occupying a position that is substantially identical to the position of a corresponding maker element previously fixed to the insert.

2. A device according to claim 1, wherein at least one, of the energy-emitting or receiving elements comprises an ultrasound energy emitter or receiver element.

3. A device according to claim 1, having a third support element comprising at least three energy-receiving or energy-emitting elements respectively capable of being mounted in positions suitable for receiving or emitting relative to the above-mentioned second support element having the energy-emitting or energy-receiving elements respectively.

4. A device according to claim 3, wherein said third support element comprises a robotic arm and wherein the positions of the energy receiver or emitter elements on said robotic arm are known, as is the position of the surgical tool relative to said robotic arm.

5. A device according to claim 3, wherein the third support element is linked to a robotic arm which receives a surgical tool.

6. A device according to claim 1, wherein the first support element and the second support element are substantially identical in shape, each support element comprising a central body designed to cooperate with the above-mentioned insert and having at least three arms extending outwardly from the central body and having in the vicinity of their free ends either at least one of the marker elements or at least one of the energy-emitting or energy-receiving elements.

7. A device according to claim 6, wherein the arms are of different lengths, so as to ensure that the positions of the marker elements or of the emitter or receiver elements are asymmetrical.

8. A device according to claim 1, wherein the insert has a fixing portion for fixing to the anatomical structure where the surgical operation is to be performed, and a portion designed to be connected to the first or second support element.

9. A device according to claim 8, wherein the insert has predetermined orientation means cooperating respectively with other predetermined orientation means disposed on the first support element or the second support element.

10. A device according to claim 1, further comprising an imaging device, and wherein said imaging device is selected from a scanner, an MRI imaging device, and a PET imaging device, with the marker elements being adapted to show up in the image obtained with the imaging device.

11. The device of claim 1, wherein said single anchoring means comprises means for anchoring said insert to an external portion of a patient's skull.

12. A device for bringing images of a body part intended to be searched or submitted to surgery to register for robotic image guided search or surgery, comprising an insert arrangeable on only a localized zone of an anatomical structure and having anchoring means for anchoring said insert directly into a bone area proximate the localized zone of an anatomical structure, said insert being designed to receive successively at least two separate support elements, namely a first support element having at least three marker elements disposed in non-aligned and spaced-apart configuration and comprising a material that shows up in an image produced with an imaging device, and a second support element having one of at least three energy emitter or receiver elements disposed in a non-aligned and spaced-apart configuration, each energy-emitter or receiver element of the second support element, when in place on the insert, in replacement of the first support element, occupying a position that is substantially identical to the position of a corresponding maker element previously fixed to the insert, said device comprising a third support element having the other of at least three energy emitter or receiver elements mounted in positions suitable for communicating with the energy emitter or receiver elements on the second support element, said third support element being linked to a robotic arm receiving a surgical tool, the positions of the energy emitter or receiver elements on said second support element being known as is the position of the surgical tool relative to said robotic arm, thereby enabling a surgeon to perform robotic image-guided search or surgery.

13. The device of claim 1, wherein said anchoring means comprises means for anchoring said insert to a patient's skull.

14. The device of claim 12, further comprising processing means for processing signals emitted by said emitter elements and then received by said receiver elements for locating the coordinates of said one of at least three energy emitter or receiver elements on said second support element in the frame of reference of the robotic arm.

15. The device of claim 14, wherein a preprocedure image showing the positions of said marker elements relative to said anatomical structure is recorded and wherein said processing means further comprises means for locating, relative to the coordinates of the marker elements on the preprocedure image, the coordinates of at least one of said robotic arm and said energy emitter or receiver elements on said second support element, whereby the position of the robotic arm relative to the anatomical structure may be determined.

16. The device of claim 15, further comprising a surgical tool affixed to said robotic arm, and a control means connected to said processing means and to said robotic arm for controlling movement of said surgical tool relative to said anatomical structure for carrying out a surgical procedure.

17. A device for bringing images of a body part intended to be searched or submitted to surgery to register for robotic image guided search or surgery, comprising at least one insert, wherein each insert is arrangeable on only a localized zone of an anatomical structure and has anchoring means for anchoring said insert into a bone area proximate the localized zone, said insert being designed to receive successively at least two separate support elements, namely a first support element having at least three marker elements disposed in non-aligned and spaced-apart configuration and comprising a material that shows up in an image produced with an imaging device, and a second support element having one of at least three energy emitter or receiver elements disposed in a non-aligned and spaced-apart configuration, each energy emitter of receiver element of the second support element when in place on the insert, in replacement of the first support element, occupying a position that is substantially identical to the position of a corresponding marker element previously fixed to the insert, said device comprising a third support element comprising the other of at least three energy emitter or receiver elements mounted for communicating with the energy emitter or receiving elements on the second support element, said third support element being linked to a robotic arm receiving a surgical tool, the positions of the energy emitter or receiver elements on said second support element being known as is the position of the surgical tool relative to said robotic arm, thereby enabling a surgeon to perform robotic image-guided search or surgery, the first support element and the second support element being substantially identical in shape, each support element comprising a central body configured to mate with the insert and having at least three arms extending outwardly from the central body, each of said arms of said first support element having in the vicinity of its free end at least one of the marker elements, and each of said arms of said second support element having in the vicinity of its free end one of said at least three energy emitter or receiver elements.

18. The device of claim 17, wherein said anchoring means comprises means for anchoring said insert to a patient's skull.

19. A device for bringing images of a body part intended to be searched or submitted to surgery to register for robotic image guided search or surgery, comprising at least one insert, wherein each insert is arrangeable on only a localized zone of an anatomical structure and has anchoring means for anchoring said insert into a bone area proximate the localized zone, said insert being designed to receive successively at least two separate support elements, namely a first support element having at least three marker elements disposed in non-aligned and spaced-apart configuration and comprising a material that shows up in an image produced with an imaging device, and a second support element having one of at least three energy emitter or receiver elements disposed in a non-aligned and spaced-apart configuration, each energy emitter of receiver element of the second support element when in place on the insert, in replacement of the first support element, occupying a position that is substantially identical to the position of a corresponding marker element previously fixed to the insert, said device comprising a third support element comprising the other of at least three energy emitter or receiver elements mounted for communicating with the energy emitter or receiving elements on the second support element, said third support element being linked to a robotic arm receiving a surgical tool, the positions of the energy emitter or receiver elements on said second support element being known as is the position of the surgical tool relative to said robotic arm, thereby enabling a surgeon to perform robotic image-guided search or surgery, the first support element and the second support element being substantially identical in shape, each support element comprising a central body configured to mate with the insert and having at least three arms extending outwardly from the central body, each of said arms of said first support element having in the vicinity of its free end at least one of the marker elements, and each of said arms of said second support element having in the vicinity of its free end one of said at least three energy emitter or receiver elements, the arms of said first support element being of different lengths and the arms of said second support elements being of different lengths, thereby insuring that the marker elements on the first support element and the one of at least three energy emitter or receiver elements on the second support element are asymmetrically positioned relative to their respective central body.

20. The device of claim 18, wherein said anchoring means comprises means for anchoring said insert to a patient's skull.

21. A method of bringing an anatomical structure of a patient into proper register for robotic image-guided surgery, the method comprising a preprocedure step of taking a preprocedure image of the anatomical structure where the surgical operation is to be performed, said anatomical structure being provided with marker elements for marking the anatomical structure and visible on said image; a second step of securing to said anatomical structure a plurality of one of energy emitter or receiver elements suitable for enabling a plurality of the other of said energy emitter or receiver elements to pick up data relating to the positions in three dimensions of said plurality of said one of the energy emitter or receiver elements; and a third step of bringing the positions of said plurality of said one of the energy emitter or receiver elements into register with the positions of the marker elements in the preprocedure image, thereby enabling a preprogrammed surgical approach to be followed, wherein:

a) said preprocedure step comprises fixing at least one registering device to said anatomical structure, said registering device comprising an insert arrangeable on only a localized zone of an anatomical structure and having anchoring means for anchoring said insert directly into a bone area proximate the localized zone of said anatomical structure, said insert being designed to receive successively at least two separate support elements, namely a first support element having at least three marker elements disposed in non-aligned and spaced-apart configuration and comprising a material that shows up in an image produced with an imaging device, and a second support element having at least three of said one of said energy emitter or receiver elements disposed in a non-aligned and spaced-apart configuration, each of said one of said energy emitter or receiver elements of the second support element, when in place on the insert, occupying a position that is substantially identical to the position of a corresponding marker element previously fixed to the insert;

b) said preprocedure step also comprises taking an image with an appropriate imaging device while said first support element is mounted on said insert, which image is stored and optionally displayed on an image display device;

c) said second step comprises replacing said first support element on said insert with said second support element so that each of said one of said energy emitter or receiver elements of the second support element is in a position that is essentially identical to a position occupied by a respective marker on said first support element when fixed to the insert during step (b);

d) providing a third support element having at least three of said other of said energy emitter or receiver elements in positions suitable for communicating with said plurality of said one of said energy emitter or receiving elements on said second support element;

e) receiving at said receiver elements energy emitted by said emitter elements and storing data corresponding to the energy received by said receiver elements;

f) processing said data stored in step (e) to determine the positions in three dimensions of said plurality of said one of said energy emitter or receiver elements on said second support element; and g) using the determined positions in three dimensions of said plurality of said one of said energy emitter or receiver elements to modify the patient's position so as to bring said plurality of said one of said energy emitter or receiver elements into register with the position of the marker elements relative to the anatomical structure based on said image stored in step (b).

22. The method according to claim 21, wherein said step (d) comprises linking the third support element to a robotic arm that receives a surgical tool.

23. The method of claim 21, wherein said method is for robotic image-guided surgery.

24. The method of claim 21, wherein said step of fixing at least one registering device comprises anchoring the insert to a skull bone.

* * * * *